US00PP08343P

United States Patent [19]

Vlielander

[11] Patent Number: Plant 8,343

[45] Date of Patent: Aug. 10, 1993

[54] KALANCHOE PLANT — MOUNT ROBSON CULTIVAR

[75] Inventor: Ike Vlielander, De Lier, Netherlands

[73] Assignee: Fides Beheer B.V., De Lier, Netherlands

[21] Appl. No.: 868,206

[22] Filed: Apr. 14, 1992

[51] Int. Cl.[5] ..... A01H 5/00

[52] U.S. Cl. ..... Plt./87.15

[58] Field of Search ..... Plt./87.15

*Primary Examiner*—James R. Feyrer

*Assistant Examiner*—Erich Veitenheimer

*Attorney, Agent, or Firm*—Burns, Doane, Swecker & Mathis

[57] ABSTRACT

A new and distinct cultivar of Kalanchoe plant named Mount Robson is provided. The plant forms attractive substantially white flowers, exhibits a strong growth habit, and is freely branched. The plant is highly floriferous, and is particularly well suited for growing as an ornamental potted plant which brightens the environment. The keeping quality of the new cultivar is good.

1 Drawing Sheet

SUMMARY OF THE INVENTION

The new variety of Kalanchoe plant was created at De Lier, The Netherlands, in a controlled environment by artificial pollination wherein two parents were crossed which previously had been studied in the hope that they would contribute the desired characteristics. The female parent (i.e., the seed parent) was an unnamed seedling designated FK 2625. The male parent (i.e., the pollen parent) was the Fortyniner Cultivar (U.S. Plant Pat. No. 5,256). The parentage of the new cultivar can be summarized as follows:

FK 2685 × Fortyniner.

The seeds resulting from the above pollination were sown and small plantlets were obtained which were physically and biologically different from each other. Selective study resulted in the identification of a single plant of the new cultivar.

It was found that the new cultivar of the present inventiton can be readily distinguished from its Fortyniner parent cultivar through the exhibition of an attractive substantially white flower coloration instead of the deep yellow flower coloration of its parent.

It has been found through careful study that the new cultivar of the present invention exhibits the following combination of characteristics:

(a) forms on a highly floriferous basis attractive substantially white flowers with numerous flowers per shoot,
(b) exhibits a strong growth habit,
(c) exhibits a freely branching character wherein shoots generally are formed at each node,
(d) is suited for production in pots having a diameter of approximately 9 to 12 cm.,
(e) is amenable to the application of a growth regulator to reduce the peduncle elongation which otherwise would be achieved,
(f) exhibits a flowering response of approximately 9½ weeks, and
(g) exhibits good keeping qualities.

The new cultivar well meets the needs of the horticultural industry, and is particularly well suited for growing as an attractive ornamental potted plant.

The new cultivar has been found to undergo asexual propagation by stem cuttings at De Lier, The Netherlands. The characteristics of the new cultivar have been found to be firmly fixed and well retained and to be strictly transmissible by such asexual propagation from one generation to another.

The new cultivar has not been observed under all possible environmental conditions to date. Accordingly, it is possible than the phenotype described herein may vary with changes in the environment such as temperature, light intensity, and day length.

The new cultivar of the present invention has been named the Mount Robson cultivar.

BRIEF DESCRIPTION OF THE PHOTOGRAPH

The accompanying photograph shows as nearly true as it is reasonably possible to make the same in a color illustration of this character, a typical specimen of the overall plant of the new cultivar wherein the attractive white blossoms, growth habit, and foliage are apparent. The plant was grown in a greenhouse at De Lier, The Netherlands, under conditions which closely approximate those generally used in commercial practice. The plant illustrated had been treated with Alar/B9 growth regulator in order to reduce peduncle elongation.

DETAILED DESCRIPTION

The chart used in the identification of the colors is that of The Royal Horticultural Society (R.H.S. Colour Chart). The color values were taken under natural light conditions. Colors in common terms also are provided in some instances. These are to be accorded their usual dictionary significance. The description is based on the observation of plants grown in a greenhouse at De Lier, The Netherlands, under conditions which closely approximate those generally used in commercial practice.

Botanical classification: *Kalanchoe blossfeldiana* cv. Mount Robson.

Parentage:

*Female parent.*—FK 2625.

*Male parent.*—Fortyniner cultivar.

Propagation: The new cultivar well holds its distinguishing characteristics through successive propagations by shoot cuttings. When operating at approximately 21° C., approximately 9 days are required for roots to form in the summer and approximately 14 days for roots to form in the winter. large thick roots commonly form.

Plant description:

*Form.*—Upright, medium-tall size, growing and scheduling practices can produce medium-sized or larger plants. The use of a growth regulator such as Alar/B9 of Bonzi is recommended so as to reduce the elongation of the peduncle length which otherwise would tend to occur.

*Growth habit.*—Strong rate of growth, generally shoots are formed at every node.

*Foliage description.*—Leaves are simple, opposite, and generally are symmetrical. Leaf size: Average. When a flowering plant is being grown in a 10½ cm. diameter pot, a fully grown leaf commonly is approximately 90 mm. in length and approximately 55 mm. in width. Leaf shape: Elliptic, the apex is acute to obtuse, and the base is acute. Leaf texture: Glabrous, coriaceous, succulent. Leaf margin: Crenate. Leaf color: On young foliage, the upper side is Green Group 137A and the under side is Green Group 137B. On mature foliage, the upper side is Green Group 137A and the under side is Green Group 137B.

Flowering description:

*Flowering habit.*—The inflorescence on each shoot is formed by dichotomous branching and starts with the opening of the terminal flower on the main axis and is followed by terminal flowers on the side branches. The opening of new buds commonly will continue over a period of 8 weeks or more. Commonly individual flowers last 2½ weeks or more following opening.

*Natural flowering season.*—November. Under controlled daylength at 25° C. in the summer the flowering time is approximately 8 weeks, and under controlled daylength at 20° C. in the winter the flowering time is approximately 11 weeks. The flowering duration commonly is influenced by the temperature, light intensity, and other growing conditions.

*Buds.*—Oblong and assume a tubular configuration as the petals mature, are sheathed with 4 green sepals, the corolla at maturity commonly is approximately 13 mm. in length at maturity, and the length of the bud commonly is approximately 16 mm.

*Flowers borne.*—Compound dichasial cymes are present on fairly long peduncles. The peduncle length is influenced by growing conditions and the application of growth regulator such as Alar/B9 or Bonzi. The peduncles commonly are up to 5 mm. in length.

*Flower quantity.*—Very floriferous with new buds continuing to develop.

*Petal shape.*—Nearly round with cuspidate apex.

*Petal coloration.*—The top side is Yellow Group 11D when opening, fading to White Group 155B to Yellow-White Group 158D to Red Group 49D; and on the under side is White Group 155D.

*Petal number.*—Four united in the corolla.

*Petal size.*—Approximately 5 mm. in length.

*Flower diameter.*—Commonly approximately 15 mm.

*Stamens.*—8 in number. The anthers are flat and elliptic in configuration. The filaments are yellow in coloration, and the pollen is yellow in coloration.

*Pistils.*—The stigmas are flat in configuration. The styles are light yellow-green in coloration. The ovaries are four-celled, and approximately 9 mm. in length.

Disease resistance: No known Kalanchoe diseases have been observed to date.

I claim:

1. A new and distinct cultivar of Kalanchoe plant characterized by the following combination of characteristics:

(a) forms on a highly floriferous basis attractive substantially white flowers with numerous flowers per shoot,
(b) exhibits a strong growth habit,
(c) exhibits a freely branching character wherein shoots generally are formed at each node,
(d) is suited for production in pots having a diameter of approximately 9 to 12 cm.,
(e) is amenable to the application of a growth regulator to reduce the peduncle elongation which otherwise would be achieved,
(f) exhibits a flowering response of approximately 9½ weeks, and
(g) exhibits an extremely good keeping qualities, substantially as herein shown and described.

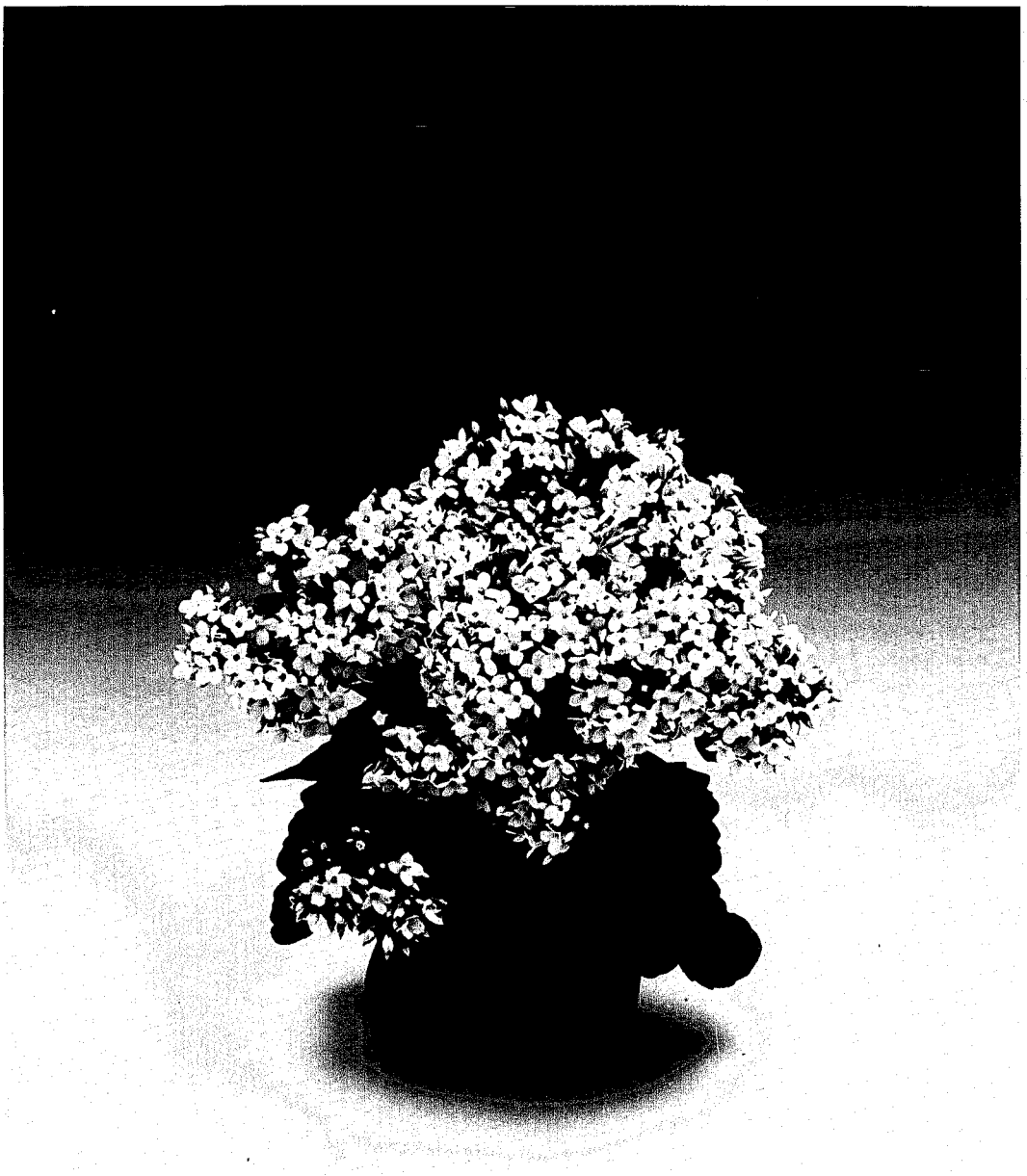

* * * * *